United States Patent
Soloman

Patent Number: 5,913,886
Date of Patent: Jun. 22, 1999

[54] BODY TEMPERATURE CONTROL SYSTEM AND METHOD OF TEMPERATURE CONTROL

[76] Inventor: Alan Soloman, 16 Fox Run Rd, Dover, Mass. 02030

[21] Appl. No.: 08/677,097

[22] Filed: Jul. 9, 1996

[51] Int. Cl.[6] .................................................. A61F 7/00
[52] U.S. Cl. ............................................................ 607/108
[58] Field of Search ................................. 607/108, 109, 607/112, 114; 602/2, 14

[56] References Cited

U.S. PATENT DOCUMENTS

| | | |
|---|---|---|
| 546,436 | 9/1895 | Springsteen . |
| 3,507,321 | 4/1970 | Palma . |
| 3,561,435 | 2/1971 | Nicholson ................................. 602/14 |
| 4,572,188 | 2/1986 | Augustine et al. . |
| 4,685,462 | 8/1987 | Olsen . |
| 5,018,521 | 5/1991 | Campbell . |
| 5,106,373 | 4/1992 | Augustine et al. . |
| 5,123,407 | 6/1992 | Dewhurst . |
| 5,184,612 | 2/1993 | Augustine . |
| 5,269,369 | 12/1993 | Faghri . |
| 5,300,101 | 4/1994 | Augustine et al. . |
| 5,300,102 | 4/1994 | Augustine et al. . |
| 5,324,320 | 6/1994 | Augustine et al. . |
| 5,336,250 | 8/1994 | Augustine . |
| 5,350,417 | 9/1994 | Augustine . |
| 5,383,918 | 1/1995 | Panetta . |
| 5,405,371 | 4/1995 | Augustine et al. . |
| 5,407,421 | 4/1995 | Goldsmith ................................. 602/14 |
| 5,411,542 | 5/1995 | Jensen . |
| 5,470,353 | 11/1995 | Jensen . |
| 5,486,206 | 1/1996 | Avery ...................................... 607/112 |

*Primary Examiner*—William E. Kamm
*Attorney, Agent, or Firm*—Wood, Phillips, VanSanten, Clark & Mortimer

[57] ABSTRACT

A system for controlling the temperature of a human body having an outer layer, a mechanism for exchanging thermal energy with a human body with a first part to be disposed between the outer layer and a surface of a human body, and a fitting mechanism at least partially disposed between the outer layer and the first part of the energy exchanging mechanism for shaping the first part of the energy exchanging mechanism to substantially conform to a surface of a human body. Also a method for controlling the temperature of a human body includes applying a mechanism for exchanging thermal energy with a human body to a surface on a human body, shaping the energy exchanging mechanism to substantially conform to a surface of a human body, and changing the temperature of a human body as an incident of activating the energy exchanging mechanism.

18 Claims, 4 Drawing Sheets

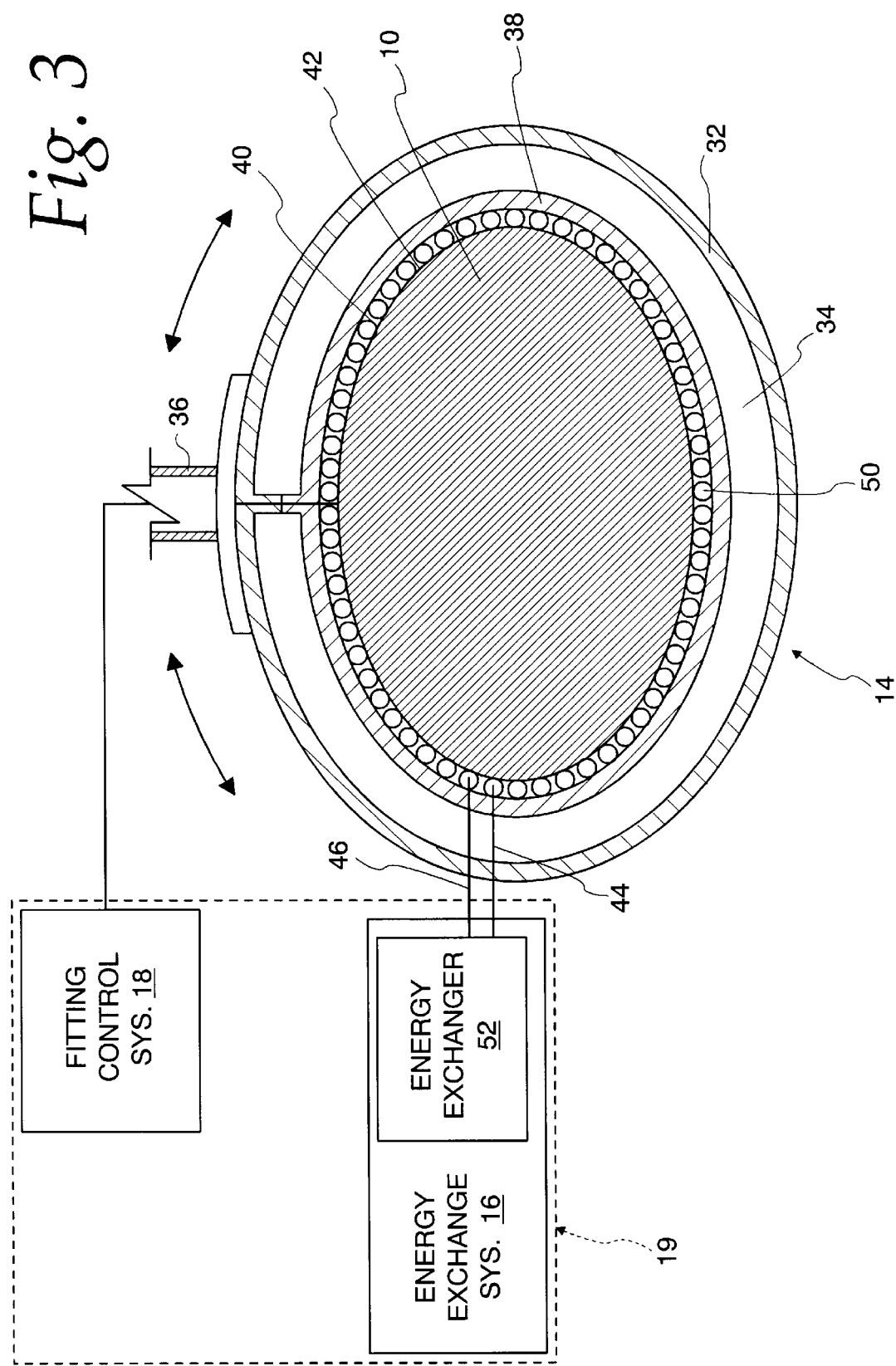

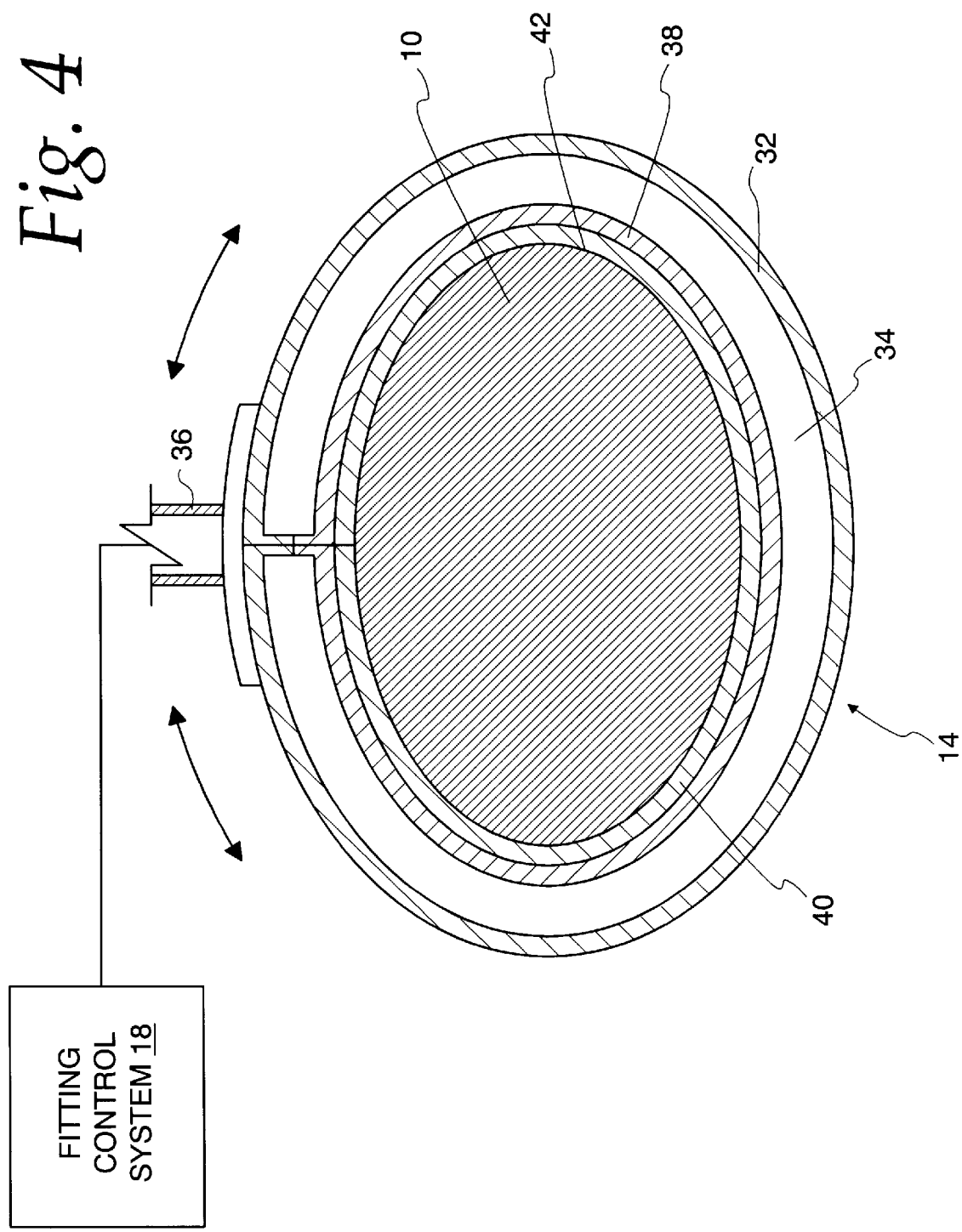

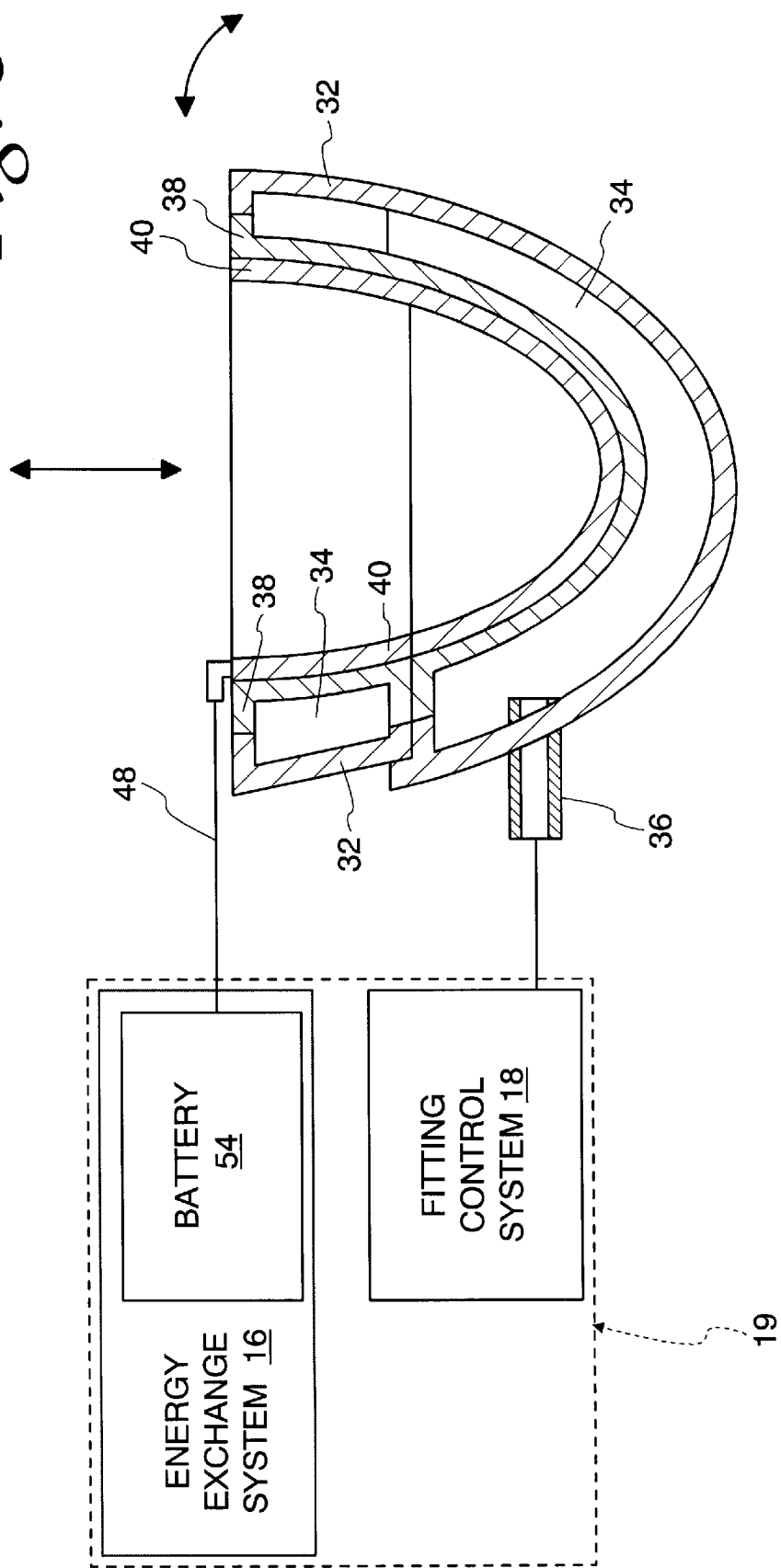

BODY TEMPERATURE CONTROL SYSTEM AND METHOD OF TEMPERATURE CONTROL

FIELD OF THE INVENTION

This invention is directed to a body temperature control system and a method of temperature control, and in particular to a body temperature control system with and a method for temperature control using a mechanism for selectively forming a close fit between a thermal energy exchanging mechanism and a surface of a human body.

BACKGROUND OF THE INVENTION

The core body temperature of a healthy human being usually remains at about 98.6 degrees F. When the core body temperature varies significantly either above or below this level, a human being can experience great suffering and damage to his or her health, possibly resulting in death. If the core body temperature drops significantly below levels compatible with health and survival, the condition is referred to as hypothermia. If the core body temperature rises significantly above levels compatible with health and survival, the condition is referred to as hyperthermia.

In its most basic form, the first aid treatment for the condition of hypothermia involves removing the affected person from the low temperature environment, and wrapping the affected person in a blanket. Similarly, basic first aid treatment for the condition of hyperthermia involves removing the affected person from the high temperature environment, and stripping the clothing off of the affected person.

Recognizing that these basic forms of first aid treatment are too crude to prevent death in serious life-threatening cases, various methods have been devised for the treatment of hypo- and hyperthermia through the use of external heating or cooling sources to raise or lower the core body temperature of the affected person. These methods are categorized generally as either direct or indirect methods of treatment.

In the direct method of treatment, the warming or cooling sources are applied directly to the core areas of the human body, such as the lungs, esophagus, and circulatory system, in an attempt to allow caloric transfer to be accomplished by conduction or convection with the body core. This method of treatment can be reasonably effective, but because of the invasive nature of the treatment procedure, this method is normally administered within a hospital setting.

Frequently, however, the person suffering from the hypo- or hyperthermic condition is located in a remote outdoor location, such as in a forest, at a beach, or on a river or lake. The person may have traveled to the remote location to enjoy some outdoor recreational activity, such as boating, swimming, mountain climbing, hiking, or jogging, or may have traveled to the remote location because their livelihood involves work in the outdoors, for example, as a logger or drill rig worker. By the time such a person suffering from either hypo- or hyperthermia arrives at the hospital, it is often too late to ensure his or her survival using the direct method of treatment described above.

In the indirect method of treatment, warming or cooling sources or fluids are applied to surface areas of the human body in an attempt to allow caloric transfer to be accomplished by conduction through the surface of the skin to the body core. Thus, theoretically, this method of treatment has the advantage over the direct method in that it is non-invasive, and therefore may more easily be performed outside the hospital setting.

However, while theoretically not requiring a hospital environment, the various devices designed to use the indirect method of treatment have often proved to be so bulky and awkward that they have not proven suitable for widespread first aid use outside of the hospital. Moreover, even when used in the hospital, these devices may be relatively ineffective. When used outside of the hospital, the effectiveness of such devices may decrease to the point that the treatment is completely ineffective.

For example, devices have been devised which circulate a warming or cooling fluid over the surface of the body in attempt to raise or lower the body core temperature. Examples of such devices can be seen in U.S. Pat. Nos. 4,572,188; 5,106,373; 5,184,612; 5,300,101; 5,300,102; 5,324,320; 5,336,250; 5,350,417; 5,383,918 and 5,405,371. These devices are bulky, require a great deal of space to set up, and are not designed to be easily used in those remote locations, such as beaches, forests, and mountains, from which a significant percentage of hypo- and hyperthermia cases originate.

Alternatively, devices have been suggested where a thermal energy exchanging mechanism, such as a plurality of tubes conducting a cooling or warming fluid, a plurality of electrical heating elements producing thermal energy electrically, or a plurality of heat sources using energy released as the product of a chemical reaction, is contained within a close fitting garment which is then pulled over or strapped tightly to a surface of a body. Examples of such devices can be seen in U.S. Pat. Nos. 546,436; 3,507,321; 4,685,462; 5,018,521; 5,269,369; 5,411,542 and 5,470,353. However, because these devices fit snugly to the surface of the body, these devices may be difficult to fit onto the affected person. Once in place, these devices may not be easily removable, and thus may impede other medical treatments necessary for the survival of the affected person.

While not directed to the treatment of hypo- or hyperthermia, warming or cooling devices have also been designed which support a thermal energy exchanging mechanism in a close-fitting relationship with a surface of a body for heating or cooling by providing a shaped or contoured padding material between an article of clothing worn by the person and the thermal energy exchanging mechanism. An example of such a device can be seen in U.S. Pat. No. 5,123,407.

However, there is no discussion in U.S. Pat. No. 5,123,407 of using such a device to treat hypo- or hyperthermia. Furthermore, in operation, the padding material is designed to maintain a predetermined contour such that the padding material does not adjust the energy exchanging mechanism to achieve the necessary continuity of contact between the energy exchanging mechanism and the surface of the body to allow for efficient treatment of hypo- or hyperthermia. Rather, the padding material generally attempts to force the underlying body surface to conform to the contours of the energy exchanging mechanism and the padding material.

Moreover, all three groups of devices fail to target the critical thermal energy transfer areas of the body. It is well documented that the most critical areas for thermal energy transfer to the body core through the skin surface are the head, neck, axilla, and groin. None of the present devices, as described above, effectively addresses the selective application of a warming or cooling source to these most critical areas of the body for the treatment of hypo- or hyperthermia.

SUMMARY OF THE INVENTION

In one form of the invention, a system for controlling the temperature of a human body has an outer layer, a mechanism for exchanging thermal energy with a human body and having a first part to be disposed between the outer layer and a surface of the human body, and a fitting mechanism at least partially disposed between the outer layer and the first part of the energy exchanging mechanism for shaping the first part of the energy exchanging mechanism to substantially conform to a surface of the human body.

The system may also have an inner layer secured at least partially to the outer layer, with the fitting mechanism at least partially disposed between the outer layer and the inner layer. Moreover, the energy exchanging mechanism may be secured at least partially to the inner layer. Moreover, the outer layer may be water resistant and the inner layer may be water permeable.

The fitting mechanism may have an inflatable bladder disposed between the outer layer and the first part of the energy exchanging mechanism.

The energy exchanging mechanism may have a thermal energy exchanger disposed in a location remote to the first part of the energy exchanging mechanism to exchange thermal energy with a working fluid, a first conduit having an inlet and an outlet, the first conduit connected at the inlet to the thermal energy exchanger and the outlet to the first part of the energy exchanging mechanism to transport a working fluid from the thermal energy exchanger to the first part, and a second conduit having an inlet and an outlet, the second conduit connected at the inlet to the first part of the energy exchanging mechanism and the outlet to the thermal energy exchanger to transport a working fluid from the first part to the thermal energy exchanger. Moreover, the energy exchanging mechanism may include a working fluid disposed within the first part of the energy exchanging mechanism, the thermal energy exchanger, and the first and second conduits. Moreover, the temperature of the working fluid at the first conduit outlet may be higher than the temperature at the second conduit inlet and the temperature at the second conduit outlet may be lower than the temperature at the first conduit inlet. Alternatively, the temperature of the working fluid at the first conduit outlet may be lower than the temperature at the second conduit inlet and the temperature at the second conduit outlet may be higher than the temperature at the first conduit inlet.

The energy exchanging mechanism may include a packet of thermal energy-releasing chemicals.

The energy exchanging mechanism may include an electrical heating element to produce thermal energy, and a source of electric energy coupled to the electrical heating element.

Moreover, the first part of the energy exchanging mechanism may include the electrical heating element.

In another aspect of the invention, a method for controlling the temperature of a human body includes the steps of applying a mechanism for exchanging thermal energy with a human body to a surface on a human body, shaping the energy exchanging mechanism to substantially conform to a surface of a human body, and changing the temperature of the human body as an incident of activating the energy exchanging mechanism.

The applying step may include applying the mechanism for exchanging thermal energy about the head, the neck, axilla, and/or the groin of a human body.

The shaping step may include securing an outer layer about a surface of a human body, placing an inflatable bladder between the outer layer and the energy exchanging mechanism, and inflating the bladder so as to substantially conform the energy exchanging mechanism to a surface of a human body. Moreover, the method may include the steps of deflating the bladder, removing the outer layer from about a surface of a human body, and removing the energy exchanging mechanism from a surface of a human body. Moreover, the method may include the step of disposing of the energy exchanging mechanism.

The temperature changing step may include removing thermal energy from a surface of a human body. Alternatively, the temperature changing step may include transferring thermal energy to a surface of a human body.

Thus, the temperature control system may provide for good contact of a thermal energy exchanging mechanism with those surfaces of a body important for thermal energy transfer with the core of the body.

The temperature control system may provide a mechanism which fits a thermal energy exchanging mechanism to a body so as to conform the thermal energy exchanging mechanism to the contours of the body.

The temperature control system may prevent continued thermal energy loss or gain from the areas important for thermal energy transfer with a core of a body so as to prevent exacerbation of the hypo- or hyperthermic condition.

The temperature control system may be adaptable to use any number of thermal energy exchanging mechanisms, including mechanisms which may be adaptable to use substances found in the surrounding environment, such as hot or cold water.

The temperature control system may have decreased size and bulk, and as an incident thereof increased portability, permitting use of the temperature control system in the home, in the workplace, or in remote locations where medical assistance is not readily available or a hospital may not be readily accessible.

The temperature control system may have a relatively small size, and as an incident decreased cost.

The temperature control system may have a reusable portion which does not come in direct contact with a body of an affected person, and a disposable portion for direct application to the surface of the body, thereby minimizing the costs of the overall system by isolating the more expensive sections of the system so that they may be used many times over, while maximizing sterility through use of a disposable section which is in contact with the surface of the body.

BRIEF DESCRIPTION OF THE DRAWINGS

FIG. 3 is a cross-sectional view of the embodiment of the present invention taken about line 3—3 in FIGS. 1 and 2 configured to use a thermal energy exchanging system using a thermal energy exchanging working fluid;

FIG. 4 is a cross-sectional view similar to that in FIG. 3 of another embodiment of the present invention including a self-contained thermal energy exchanging system, for example, packets releasing thermal energy as an incident of a chemical reaction; and FIG. 5 is a cross-section view of the embodiment of the present invention taken about line 5—5 in FIGS. 1 and 2, configured to use an electrical thermal energy exchanging system with the human body absent to better show the details of this embodiment.

DESCRIPTION OF THE PREFERRED EMBODIMENTS

According to one aspect of the present invention, a body temperature control system includes a survival suit preferably with an inflatable bladder and a thermal energy, or heat, exchanging mechanism. Preferably, the survival suit is to be applied to the head, neck, axilla, and/or groin of an affected person. At least part of the thermal energy exchanging system is preferably fitted inside an outer layer of the survival suit, with the inflatable bladder preferably between the outer layer and the thermal energy exchanging system. By inflating the bladder, the thermal energy exchanging mechanism is preferably forced inward towards the surfaces of the body over which the survival suit is applied so as to conform to the contours of these surfaces. In this way, the thermal energy exchanging mechanism efficiently effects thermal energy exchange between the energy exchanging mechanism and the core of the body of the affected person.

Figure 1:
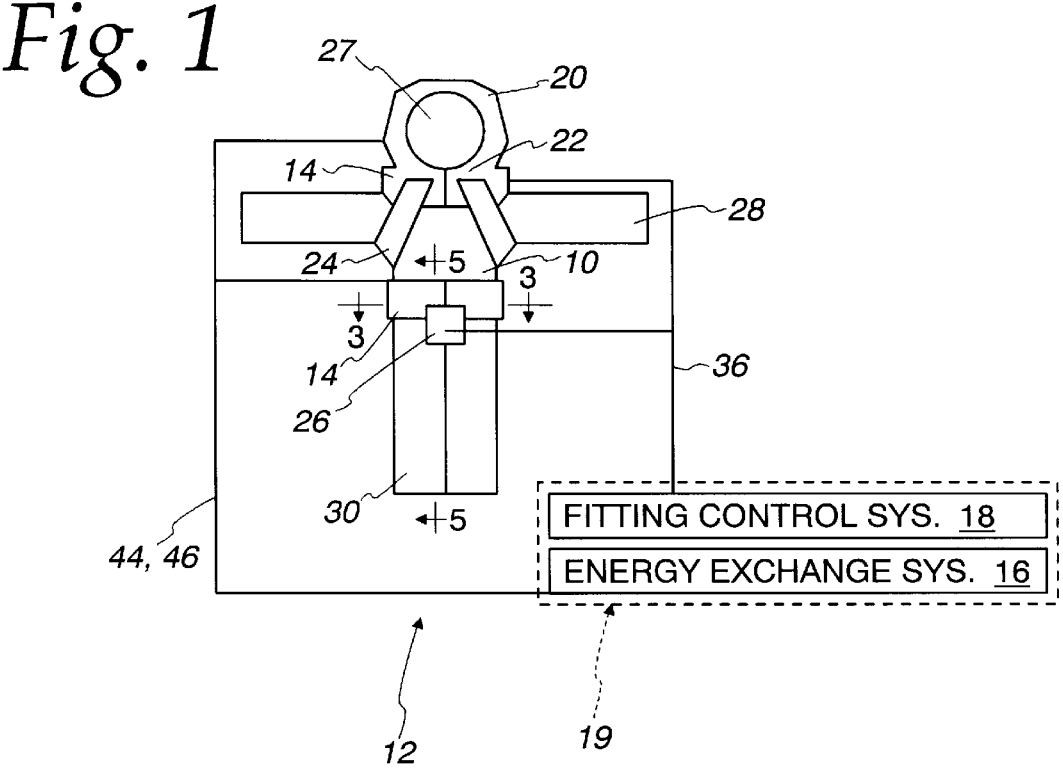
FIG. 1 is a frontal schematic view of an embodiment of the present invention shown as applied to a human body.
Figure 2:
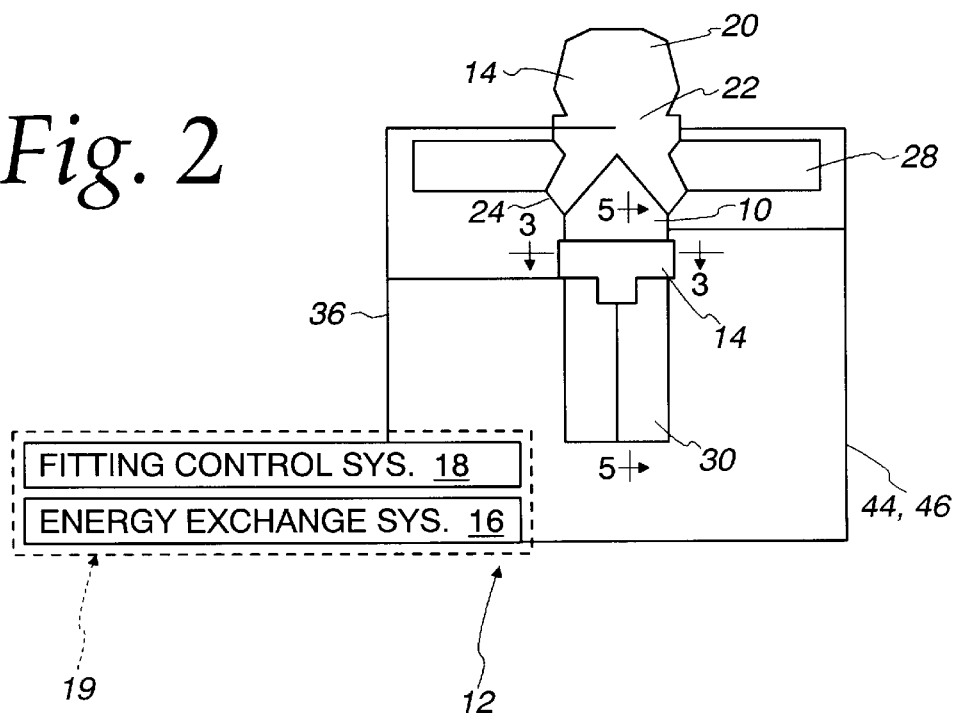
FIG. 2 is a rear schematic view of an embodiment of the present invention shown as applied to a human body.

Thus, in one embodiment of the present invention as shown in FIGS. 1 and 2, a human body 10 is fitted with a temperature control system 12 which preferably includes a two-piece survival suit 14, a thermal energy or heat exchanging mechanism/system 16, and a fitting control system 18. While the survival suit 14 is shown preferably as two pieces, the survival suit 14 may be any number of pieces or one piece, and may cover any part of, or the entirety of, the body 10. Preferably, the thermal energy exchanging system 16 and the fitting control system 18 are assembled together in a case 19 for ease of transport.

In use, the survival suit 14 is preferably fitted to the body 10 so that one piece covers the head 20, the neck 22 and axilla 24, and the second piece covers the groin 26. The survival suit 14 may be secured about the body 10 by means of drawstrings (for instance, for securing the suit 14 about the face 27), straps, snaps, VELCRO-type fasteners, or buttons. Alternatively, the suit 14 may have zippers at side-facing seams, which can be zipped together to ensure that the suit 14 is secured to the body 10. As a further alternative, the suit may be made as two individual pieces which are separately and loosely fitted over the head 20 and/or around and about the arms 28 and/or the legs 30. Once the suit 14 is fitted about the head 20, the neck 22, the axilla 24, and the groin 26, the fitting control system 18 is used to force the thermal energy exchanging system 16 into a close fitting relationship with the body 10.

Referring to FIGS. 3–5, it can be seen that the suit 14 is manufactured with several layers. An outermost layer 32 protects the inner layers and serves to support the inner layers when the fitting control system 18 is activated to hold the thermal energy exchanging system 16 in a close fitting relationship with the body 10. Preferably, the outer layer 32 is fabricated with a water-resistant outer surface.

Immediately interior to the outer layer 32 is an adjustable fitting layer 34, which is part of the fitting control system 18 and is preferably connected via a tube 36 to the remainder of the fitting control system 18. Preferably, the adjustable fitting layer 34 may be a removable, inflatable bladder, or bladders, which may be reversibly inflated or deflated by a control portion of the fitting control system 18 through the use of a working fluid, such as air or water. The adjustable fitting layer 34 may be permanently affixed to the outer layer 32.

The fitting control system 18 described above is merely the preferred embodiment of the fitting control system 18 of the present invention. Alternatively, the adjustable fitting layer 34 may be inflated through the use of a material, such as a foam material, which will harden or stiffen with time to hold all or a portion of the thermal energy exchanging system 16 in a more permanent and less reversible close fitting relationship with the body 10. As a further alternative, the adjustable fitting layer 34 may be made up of a plurality of inflated air cells, which cells are placed between the outer layer 34 and a portion of the thermal energy exchanging system 16 before or after the outer layer 34 is secured about the body 10 to force the portion of the thermal energy exchanging system 16 into a close fitting relationship with the body 10. As yet another alternative, the adjustable fitting layer 34 may consist, in whole or in part, of a plurality of drawstrings, which can be passed around and drawn together about at least a portion of the thermal energy exchanging system 16 to force the thermal energy exchanging system 16 into a close fitting relationship with the body 10. As yet a still further alternative, the plurality of drawstrings may make up all or part of the outermost layer 32, serving to protect the inner layers and to support the inner layers when the fitting control system 18 thus configured is used to hold at least part of the thermal energy exchanging system 16 in a close fitting relationship with the body 10.

Interior to the adjustable fitting layer 34 is a liner 38 which separates a preferably disposable thermal energy exchanging layer or liner 40, which is part of the thermal energy exchanging system 16, from the adjustable fitting layer 34. Preferably, the liner 38 is attached at one or more points along the seam of the outermost layer 32 to support the adjustable fitting layer 34 therebetween. Additionally, the liner 38 may be made as having either a water-permeable or a water-resistant inner surface. In cases of hyperthermia, where it is desirable to wick away the moisture from the body 10, for example, it may be preferable to incorporate a water-permeable surface into the liner 38.

The thermal energy exchanging layer 40 is held substantially in contact with the surface 42 of the body 10, preferably along every point of the thermal energy exchanging layer 40. The substantial conformity of the thermal energy exchanging layer 40 to the surface 42 of the body 10 is caused by inflating the fitting layer 34 against the resistance of the outer layer 32, which has been previously loosely secured about the body 10 at the head 20, the neck 22, the axilla 24 and the groin 26.

Preferably, the adjustable fitting layer 34 is substantially shapeless, without significant structural rigidity as to a given shape or contour. As an incident of the lack of prominent contours in the adjustable fitting layer 34, the inflation of the adjustable fitting layer 34 forces the energy exchanging layer 40 to conform to the contours of the surface 42, rather than attempting to cause the surface 42 to conform to the contours of the energy exchanging layer 40 or the fitting layer 34. The thermal energy exchanging layer 40 may be prevented from creasing, bending, slipping or gathering within the liner 38 by attaching the thermal energy exchanging layer 40 to the liner 38 by straps, snaps, VELCRO-type fasteners, or netting, for example.

The remainder of the thermal energy exchanging system 16 shown in FIGS. 1–3 and 5 is preferably external to the survival suit 14. Preferably, the remainder of the thermal energy exchanging system 16 communicates with the thermal energy exchanging layer 40, for example, via tubes 44, 46 for the fluid system shown in FIG. 3 or wires 48 for the electrical system shown in FIG. 5, although the invention may include other thermal energy exchanging mechanisms, such as ultrasound. Alternatively, the thermal energy exchanging system 16 may be disposed entirely within the thermal energy exchanging layer 40, for example, in the form of heat-releasing packets which produce thermal energy based on a chemical reaction within the packet (FIG. 4).

In one embodiment of the thermal energy exchanging system 16, shown in FIG. 3, the thermal energy exchanging layer 40 is preferably made up of a thermal energy exchanging tube 50 which coils back and forth through the layer in a series of compressed S-curves. Tubes 44, 46 connect the thermal energy exchanging tube 50 with the remainder of the thermal energy exchanging system 16 and transport a working fluid, such as a liquid or a gas, between the thermal energy exchanging layer 40 and the remainder of the thermal energy exchanging system 16 which is disposed remotely to the human body 10, and includes a thermal energy exchanger 52, such as a tube-and-fin heat exchanger, as is well known in the art. According to methods known to those of skill in the art, the working fluid is transported through one of the tubes 44, 46 to the thermal energy exchanging tube 50 in the thermal energy exchanging layer 40 wherein thermal energy is either removed from or transferred to the working fluid to maintain the desired temperature of the human body 10. After passing through the entire length of the thermal energy exchanging tube 50, the working fluid is transported through the other of the tubes 44, 46 to the remainder of the thermal energy exchanging system 16, wherein thermal energy is either transferred to or removed from the working fluid by the thermal energy exchanger 52, whichever is appropriate to maintain the desired temperature of the human body 10.

If it is desired to warm the human body 10, then temperature of the working fluid entering the thermal energy exchanging tube 50 from the tube 44, for example, should be higher than the temperature of the working fluid discharging from the thermal energy exchanging tube 50 into the tube 46, and the temperature of the working fluid entering the thermal energy exchanger 52 from the tube 46 should be lower than the temperature of the working fluid discharging into the tube 46. Conversely, if it is desired to cool the human body 10, then the temperature of the working fluid entering the thermal energy exchanging tube 50 from the tube 44, for example, should be lower than the temperature of the working fluid discharging from the thermal energy exchanging tube 50 into the tube 46, and the temperature of the working fluid entering the thermal energy exchanger 52 from the tube 46 should be higher than the temperature of the working fluid discharging into the tube 46.

In another embodiment of the thermal energy exchanging system 16, shown in FIG. 5, the thermal energy exchanging layer 40 preferably includes an electrical heating element made of an electrically conductive material which emits thermal energy when a current is passed through the material. In this embodiment, the thermal energy exchanging layer 40 is connected via wires 48 to the remainder of the thermal energy exchanging system 16, including a source of electrical energy, such as battery 54. When the battery 54 is coupled to the thermal energy exchanging layer 40, the current passing through the thermal energy exchanging layer 40 causes the electrically conductive material to emit thermal energy.

In operation, the survival suit 14 is fitted to the head 20, neck 22, axilla 24 and/or groin 26 of the body 10 of a person suffering from either a hypothermic or hyperthermic condition. Preferably, the survival suit 14 is secured loosely around the body 10 with the adjustable fitting layer 34, contained between the outer layer 32 and the liner 38, not yet inflated, although the suit 14 alternatively may be secured about the body 10 with the adjustable fitting layer 34 fully inflated. If the adjustable fitting layer 34 is not inflated when the suit 14 is secured about the body 10, then the energy exchanging layer 40 may be at least partially separated from the surface 42 of the body 10.

Upon inflation of the adjustable fitting layer 34, the energy exchanging layer 40 is forced inwards against the surface 42 of the body 10. The adjustable fitting layer 34 forces the energy exchanging layer into substantial conformity with the surface 42. At this time, the energy exchanging system 40 may be activated, or, alteratively, the energy exchanging system could have been activated at the time the suit 14 was applied to the body 10.

To remove the suit 14, preferably all that is required is to remove the working fluid from the adjustable fitting layer 34, thereby deflating the layer. Alternatively, if a fitting layer working fluid has been used that will harden or stiffen with time so as to maintain the close fit between the heat exchanging layer 40 with the surface 42, the snaps, straps, zipper or other devices used to hold the outer layer 32 will need to be unfastened so that the suit 14 can be removed from the affected person undergoing treatment. As yet a further alternative, the adjustable fitting layer 34 may be removed from the suit 14.

These embodiments of the present invention may have the advantage of light weight and compactability, and thus good portability and a wider range of uses or applications than previous devices, whether those new uses or applications would be in remote locations with boaters, swimmers and hikers, or in the home with persons experiencing febrile illness or exposure to acute temperature extremes. These embodiments of the present invention may also have the advantage of adaptability to any number of different thermal energy exchanging systems 16, such as forced air, water gradient, chemical packets, electrical, and ultrasound systems.

Still other aspects, objects, and advantages of the present invention can be obtained from a study of the specification, the drawings, and the appended claims.

I claim:

1. A system for controlling the temperature of a human body, the system comprising:

an outer layer;

a thermal energy exchange system having a first part to be disposed between the outer layer and a surface of a human body; and an adjustable fitting assembly attachable to at least one of a head, neck, axilla and groin of a human body at least partially disposed between the outer layer and the first part of the thermal energy exchange system for shaping the first part of the thermal energy exchange system to substantially conform to a surface of at least one of a head, neck, axilla and groin of a human body to thereby permit substantially enough thermal energy exchange between the thermal energy exchange system and an area of the at least one of the head, neck, axilla and groin of a human body to change core temperature of a human body on which the system is used from one of a hypo- and a hyperthermia conditions.

2. The system according to claim 1, further comprising:

an inner layer secured at least partially to the outer layer, the adjustable fitting assembly at least partially disposed between the outer layer and the inner layer.

3. The system according to claim 2, wherein the thermal energy exchange system is secured at least partially to the inner layer.

4. The system according to claim 2, wherein the outer layer is water-resistant and the inner layer is water-permeable.

5. The system according to claim 1, wherein the adjustable fitting assembly further comprises an inflatable bladder disposed between the outer layer and the first part of the thermal energy exchange system.

6. The system according to claim 1, wherein the energy exchanging means further comprises:

a thermal energy exchanger disposed in a location remote to the first part of the energy exchanging means to exchange thermal energy with a working fluid;

a first conduit having an inlet and an outlet, the first conduit connected at the inlet to the thermal energy exchanger and the outlet to the first part of the energy exchanging means to transport a working fluid from the thermal energy exchanger to the first part; and a second conduit having an inlet and an outlet, the second conduit connected at the inlet to the first part of the energy exchanging means and the outlet to the thermal energy exchanger to transport a working fluid from the first part to the thermal energy exchanger.

7. The system according to claim 6, further comprising a working fluid disposed within the first part of the energy exchanging means, the thermal energy exchanger, and the first and second conduits.

8. The system according to claim 7, wherein the temperature of the working fluid at the first conduit outlet is higher than the temperature at the second conduit inlet and the temperature at the second conduit outlet is lower than the temperature at the first conduit inlet.

9. The system according to claim 7, wherein the temperature of the working fluid at the first conduit outlet is lower than the temperature at the second conduit inlet and the temperature at the second conduit outlet is higher than the temperature of the first conduit inlet.

10. The system according to claim 1, wherein the thermal energy exchange system further comprises a packet of thermal energy-releasing chemicals.

11. The system according to claim 1, wherein the energy exchanging means further comprises:

an electrical heating element to produce thermal energy; and a source of electric energy coupled to the electrical heating element.

12. The system according to claim 11, wherein the first part of the energy exchanging means comprises the electrical heating element.

13. A method for controlling the temperature of a human body, the method comprising the steps of:

applying a thermal energy exchange system about at least one of a head, a neck, axilla, and a groin of a human body;

shaping the thermal energy exchange system to substantially conform to a surface of a human body;

activating the thermal energy exchange system; and changing the temperature of a human body as an incident of activating the thermal energy exchange system.

14. The method according to claim 13, wherein the shaping step comprises:

securing an outer layer about a surface of a human body;

placing an inflatable bladder between the outer layer and the thermal energy exchange system; and inflating the bladder so as to substantially conform the thermal energy exchange system to a surface of a human body.

15. The method according to claim 14, further comprising after the step of changing the temperature of a human body the steps of:

deflating the bladder;

removing the outer layer from about a surface of a human body; and removing the thermal energy exchange system from a surface of a human body.

16. The method according to claim 15, further comprising the step of disposing of the thermal energy exchange system.

17. The method according to claim 13, wherein the temperature changing step further comprises removing thermal energy from a surface of a human body.

18. The method according to claim 13, wherein the temperature changing step further comprises transferring thermal energy to a surface of a human body.

* * * * *